United States Patent [19]

Arrigoni-Martelli

[11] 4,409,222

[45] Oct. 11, 1983

[54] PINACIDIL-DIURETIC PREPARATION FOR TREATING HYPERTENSION OR CONGESTIVE HEART FAILURE

[75] Inventor: Edoardo Arrigoni-Martelli, Birkerød, Denmark

[73] Assignee: Leo Pharmaceutical Products Ltd. A/S (Lovens Kemiski Fabrik Produktionsaktieselskab), Ballerup, Denmark

[21] Appl. No.: 363,934

[22] Filed: Mar. 31, 1982

[30] Foreign Application Priority Data

Apr. 15, 1981 [GB] United Kingdom ................. 8111986

[51] Int. Cl.$^3$ .................... A61K 31/505; A61K 31/44
[52] U.S. Cl. ..................................... 424/251; 424/263
[58] Field of Search ............................... 424/263, 251

[56] References Cited

U.S. PATENT DOCUMENTS 4,057,636 11/1977 Petersen .............................. 424/263

OTHER PUBLICATIONS

Petersen, H. et al., *J. Med. Chem.*, 21(8), 773–781 (1978).
Arrigoni–Martelli, E. et al., *Experientia*, 36, 445–447 (1980).
International Nonproprietary Names for Pharmaceutical Substances, Cumulative List 6, WHO, Geneva, 1982, p. 244.
Chemical Abstracts Registry Handbook, 1976 Supplement, p. 2011 Re.

*Primary Examiner*—Richard A. Schwartz
*Attorney, Agent, or Firm*—Cushman, Darby & Cushman

[57] ABSTRACT

The present invention relates to a pharmaceutical preparation containing as the vasodilator N"-cyano-N-4-pyridyl-N'-1,2,2-trimethylpropylguanidine and as the diuretic active component a compound selected from the group consisting of the thiazide or thiazide-like type diuretics and loop diuretics.

The combination is valuable in the treatment of mammals, including man, suffering e.g. from hypertension or congestive heart failure.

14 Claims, No Drawings

PINACIDIL-DIURETIC PREPARATION FOR TREATING HYPERTENSION OR CONGESTIVE HEART FAILURE

The present invention relates to a pharmaceutical preparation containing as one therapeutically active component the vasodilator N"-cyano-N-4-pyridyl-N'-1,2,2-trimethylpropylguanidine (in the following also designated P 1134) and as another therapeutically active component a diuretic, either of the thiazide or thiazide-like type, or a loop diuretic, to methods of preparing said preparation, to dosage units thereof, and to methods of treating patients using said preparation, in particular in the form of said dosage units thereof.

The present preparations are valuable in the treatment of mammals, including man, suffering e.g. from hypertension or congestive heart failure.

U.S. Pat. No. 4,057,636 describes a number of antihypertensive compounds having the formula

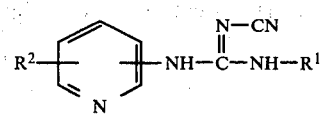

or the tautomeric forms thereof in which the $R^1$-substituted cyano-guanidyl radical is placed in the 2-, 3- or 4-position of the pyridine ring, and in which $R^1$ stands for a straight or branched, saturated or unsaturated, aliphatic hydrocarbon radical having from 1 to 8 carbon atoms, a cycloalkyl or cycloalkenyl radical having from 3 to 7 carbon atoms, an aryl or an aralkyl radical, and $R^2$ stands for hydrogen, halogen, hydroxy, lower alkyl or alkoxy radicals; which have been shown to exert an antihypertensive effect in various animal species when administered enterally or parenterally.

Among the compounds described and claimed in U.S. Pat. No. 4,057,636, P 1134 has surprisingly shown a markedly prolonged activity when used in the clinic in the treatment of hypertension which makes P 1134 particularly useful for this purpose. Specifically, the monohydrate of P 1134 has turned out to be useful for pharmaceutical preparations and dosage units thereof for clinical practice.

Its profile of activity shows the characteristics of a peripheral vasodilator, i.e. that the reduction of the elevated blood pressure is achieved through a direct effect on the vascular smooth muscles.

Patients treated with vasodilators will as a rather common side effect develop fluid retention, a side effect which is also seen in a number of patients treated with P 1134. Such fluid retention will in many instances reduce the antihypertensive effect of the vasodilator therapy.

According to the invention, however, the present combination has been shown to be very advantageous in the treatment of hypertension and congestive heart failure as it obviates possible side effects in the form of fluid retention and shows a valuable additive or even synergistic effect as far as the reduction of the blood pressure is concerned.

In fact, clinical trials have surprisingly shown that by administering a preparation according to the invention the desired lowering of the blood pressure will be obtained when P 1134 is used in amounts typically ranging between 10 and 200 mg/day, corresponding to, in adult human patients, from approximately 0.15 to 3 mg/kg body weight/day, without evidence of fluid retention.

Such a combination is further advantageous by showing a less pronounced degree of tachycardia than the previously known combinations of a vasodilator and a diuretic, e.g. combinations of the vasodilators hydralazine, guancydine, or minoxidil, with diuretics (Antihypertensive Agents, editor Franz Gross, Springer Verlag, 1977).

It is well known from the literature that reduction of elevated arterial blood pressure obtained by treatment with a vasodilator is accompanied by a reflex compensatory increase in heart rate which in most cases need to be counteracted by a concomitant administration of a β-blocking agent.

Surprisingly, it has been found that in patients given doses of P 1134 causing a significant fall of the blood pressure, only a minimal increase in the heart rate took place so that concomitant administration of β-blockers was usually not needed.

The use of the combination of the invention therefore makes it possible to avoid administering a third active ingredient, namely a β-blocker, in most cases of mild to moderate hypertension. If, in case of severe hypertension, a β-blocker has to be used, the dose of this can be smaller than in combination with other vasodilators, and will therefore result in fewer side effects.

P 1134 is a base capable of forming salts with acids among which may be mentioned the pharmaceutically acceptable non-toxic hydrochloric and hydrobromic acid, phosphoric acid, sulfuric acid, nitric acid, p-toluenesulfonic acid, methanesulfonic acid, formic acid, acetic acid, propionic acid, citric acid, tartaric acid, maleic, and pamoic acid, this list not to be considered limiting the scope of the present invention.

In the combinations of the invention, P 1134 may be used as such or in the form of a salt as mentioned above.

Among the diuretics of the thiazide type which may be used in the present combinations, mentioned may be made of hydroflumethiazide, bendroflumethiazide, chlorothiazide, cyclothiazide, hydrochlorothiazide, trichloromethiazide, cyclopenthiazide, and polythiazide, and of the thiazide-like type mention may be made of clopamide, quinethazone, mefruside, and chlorthalidone. Among the loop diuretics, mention may be made of furosemide, bumetanide, piretamide, ethacrynic acid, and indacrinone. The above enumeration shall only be considered illustrative for and not limiting the scope of the present invention.

It is an advantageous feature of the combined therapy with P 1134 and a diuretic that an antihypertensive effect, even in severe cases, is obtainable with low doses of P 1134.

Thus, it is one object of the present invention to provide a pharmaceutical preparation which is useful in the general treatment of patients suffering from e.g. hypertension or congestive heart failure.

With this object in view, the preparation of the invention contains as one active component one member selected from the group consisting of P 1134 and its salts with non-toxic, pharmaceutically acceptable acids, and as another active compound a diuretic, together with solid, semisolid, or liquid pharmaceutical carriers and/or auxiliary agents.

Said preparation should contain at least 0.1% and preferably more than 1% in total of the therapeutically active compounds and can be worked up in a manner known per se to various pharmaceutical forms of presentation, such as tablets, pills, dragees, capsules, sustained release tablets, suspensions, suppositories, injection medicine, containing the vasodilator and the diuretic used according to the invention, mixed with carriers and/or auxiliary agents.

Pharmaceutically acceptable, non-toxic organic or inorganic, solid, semisolid or liquid carriers and/or auxiliary agents suitable for oral, or enteral administration can be used to make up compositions containing the present compounds. Gelatine, sugars and sugar alcohols, starches, starch derivatives, cellulose and cellulose derivatives, calcium or magnesium stearate, talc, naturally occurring or modified vegetable and animal fats and oils, mineral oils, gums, polyalkylene glycols, polyvinyl derivatives, buffers, organic acids, carbonates, or other known carriers and/or auxiliary agents for medicaments are all suitable.

Another object of the invention resides in the selection of suitable doses of the components which doses can be administered so that the desired activity is achieved without simultaneous secondary effects.

According to the invention, the diuretic is used in the amounts usually applied when treating hypertension, e.g. between 0.5 and 2000 mg/day, depending upon the actual diuretic used, whereas P 1134 preferably is used in daily amounts between 10 mg and 200 mg.

In the human therapy, the components can conveniently be administered (to adults) in dosage units containing not less than 5 mg and up to 50 mg, preferably from 10 mg to 25 mg, of P 1134, either as such or in the form of a salt, as calculated in its free form, and from 0.1 to 1000 mg, of the diuretic, the amount depending upon the actual diuretic used.

By the term "dosage unit" is meant a unitary, i.e. a single dose which is capable of being administered to a patient, and which may be readily handled and packed, remaining as a physically stable unit dose comprising either the active material as such, or a mixture of it with solid, semisolid or liquid pharmaceutical carriers and/or auxiliary agents.

In the form of dosage units, the preparation may be administered once or more times a day at appropriate intervals, always depending, however, on the condition of the patient, and in accordance with the prescription made by the medical practitioner.

A daily dose of the preparation of the invention will typically contain from 0.15 to 3 mg/kg body weight of P 1134, and from 0.01 to 30 mg/kg body weight of the diuretic depending upon the actual compound used; thus, an adult human patient will typically receive per day from 10 to 200 mg of P 1134 and from 0.5 to 2000 mg of the diuretic.

In the continuous therapy tablets or capsules may be the appropriate form of pharmaceutical preparation. The long-lasting effect of P 1134 can be further supported by using sustained release formulations.

The invention also includes the treatment of mammals, including man, suffering from hypertension and related conditions, with the preparation of the invention in therapeutically effective doses. It shall be understood, however, that in such treatment according to the invention the diuretic and the vasodilator selected from the group of P 1134 and its salts may optionally be administered together or separately, simultaneously or with intervals, and in any adequate pharmaceutical form of presentation, preferably in the doses aforesaid.

The invention will now be described by the following examples which are only illustrative and are not to be limiting the invention.

EXAMPLE 1

| Tablet, disintegrating | |
| --- | --- |
| P 1134 monohydrate | 100 g |
| Bendroflumethiazide | 25 g |
| Lactose | 1000 g |
| Corn starch | 639 g |
| Methylcellulose aqueous solution 4% | 400 ml |
| Magnesium stearate | 20 g |

Mix P 1134 monohydrate, bendroflumethiazide, lactose, and corn starch in a high-speed mixer. Moisten the powder with the methylcellulose solution until it is granular. Then dry it in a fluid bed dryer at 50° C. Pass the dried granulate through a sieve with 0.7 mm apertures and finally mix the granulate with magnesium stearate in a tumble mixer.

Press 10,000 tablets with a target weight of 0.18 g using circular punches with 8 mm diameter.

Each disintegrating tablet contains 10 mg of P 1134 monohydrate and 2.5 mg of bendroflumethiazide.

EXAMPLE 2

| Tablet, slowly disintegrating | |
| --- | --- |
| P 1134 monohydrate | 200 g |
| Bendroflumethiazide | 25 g |
| Lactose | 1435 g |
| Stearol, atomized | 170 g |
| Magnesium stearate | 20 g |

Mix P 1134 monohydrate, bendroflumethiazide, lactose, and atomized stearol in a high speed mixer. Slug the powder mixture in a roller compactor and mill the slugs to granules passing a sieve with 0.7 mm apertures. Mix the granulate with magnesium stearate and press 10,000 tablets with target weight 185 mg using flat, circular punches with 8 mm diameter.

Each slow-disintegrating tablet contains 20 mg of P 1134 monohydrate and 2.5 mg of bendroflumethiazide.

EXAMPLE 3

| Two layer tablet One layer quickly disintegrating, one layer slowly disintegrating | |
| --- | --- |
| Quickly disintegrating layer: | |
| Bendroflumethiazide | 25 g |
| Lactose, anhydrous | 320 g |
| Sta-Rx 1500 | 150 g |
| Silicone dioxide, colloidal | 2.5 g |
| Magnesium stearate | 2.5 g |
| Slowly disintegrating layer: | |
| P 1134 monohydrate | 150 g |
| Lactose | 1050 g |
| Glycerylmonostearate, atomized | 200 g |
| Magnesium stearate | 150 g |

Benadroflumethiazide, anhydrous lactose, Sta-Rx 1500, colloidal silicone dioxide, and magnesium stearate are sieved through 0.7 mm apertures and are mixed for 15 minutes in a tumble mixer.

P 1134 monohydrate, lactose, and glyceryl monostearate are mixed for 15 minutes in a tumble mixer, and slugged in a roller compactor and milled to granules passing a sieve with 0.7 mm apertures. The slugged granules are mixed with magnesium stearate in a tumble mixer.

Press 10,000 tablets with a circular punch of 8 mm diameter. Use a target weight of 155 mg of the slowly disintegrating layer and 50 ml of the quickly disintegrating layer.

Each two-layer tablet contains 2.5 mg of bendroflumethiazide in the quickly disintegrating layer and 15 mg of P 1134 monohydrate in the slowly disintegrating layer.

EXAMPLE 4

| Tablet, disintegrating | |
|---|---|
| P 1134 monohydrate | 100 g |
| Bumetanide | 2.5 g |
| Lactose | 1000 g |
| Corn starch | 639 g |
| Methylcellulose aqueous solution 4% | 400 ml |
| Magnesium stearate | 20 g |

Mix P 1134 monohydrate, bumetanide, lactose, and corn starch in a high-speed mixer. Moisten the powder with the methylcellulose solution until it is granular. Then dry it in a fluid bed dryer at 50° C. Pass the dried granulate through a sieve with 0.7 mm apertures and finally mix the granulate with magnesium stearate in a tumble mixer.

Press 10,000 tablets with a target weight of 0.177 g using circular punches with 8 mm diameter.

Each disintegrating tablet contains 10 mg of P 1134 monohydrate and 0.25 mg of bumetanide.

EXAMPLE 5

| Tablet, slowly disintegrating | |
|---|---|
| P 1134 monohydrate | 200 g |
| Furosemide | 400 g |
| Lactose | 1435 g |
| Stearol, atomized | 170 g |
| Magnesium stearate | 20 g |

Mix P 1134 monohydrate, furosemide, lactose, and atomized stearol in a high speed mixer. Slug the powder mixture in a roller compactor and mill the slugs to granules passing a sieve with 0.7 mm aperatures. Mix the granulate with magnesium stearate and press 10,000 tablets with target weight 222 mg using flat, circular punches with 8 mm diameter.

Each slow-disintegrating tablet contains 20 mg of P 1134 monohydrate and 40 mg of furosemide.

What we claim is:

1. A pharmaceutical preparation for treating hypertension or congestive heart failure consisting essentially of an effective amount of a mixture of N"-cyano-N-4-pyridyl-N'-1,2,2-trimethylpropylguanidine and a diuretic, the two active components being used as such or, if appropriate, in the form of atoxic salts thereof.

2. A preparation as claimed in claim 1, in which the diuretic is a thiazide or thiazide-like diuretic.

3. A preparation as claimed in claim 1, in which the diuretic is a loop diuretic.

4. A preparation as claimed in claim 1, in which the diuretic is bendroflumethiazide.

5. A preparation as claimed in claim 1, in which the diuretic is hydroflumethiazide.

6. A preparation as claimed in claim 1, in which the diuretic is bumetanide.

7. A preparation as claimed in claim 1, in which the diuretic is furosemide.

8. A preparation according to claim 1 in dosage unit form.

9. A pharmaceutical preparation according to claim 8 for the treatment of patients suffering from hypertension or congestive heart failure which comprises as an active ingredient from not less than 5 mg and up to 50 mg of N"-cyano-N-4-pyridyl-N'-1,2,2-trimethylpropylguanidine, as such or as an atoxic salt thereof, and as a further active ingredient from 0.1 to 1000 mg of a diuretic, together with pharmaceutically acceptable, nontoxic carriers and/or auxiliary agents.

10. A pharmaceutical preparation according to claim 9 in the form of tablets, pills, capsules, or powder for the oral treatment of patients suffering from hypertension or congestive heart failure.

11. A method of treating mammals, including man, suffering from hypertension or congestive heart failure, which comprises administering to the patient an effective amount of a preparation according to claim 1.

12. A method according to claim 11 using a preparation in dosage unit form according to claim 8.

13. A method for the treatment of hypertension or congestive heart failure in mammals, including man, comprising simultaneous administration to a host suffering from said illness a therapeutically acceptable amount of N"-cyano-N-4-pyridyl-N'-1,2,2-trimethylpropylguanidine and a therapeutically acceptable amount of a diuretic as specified in claim 1.

14. A method for the treatment of hypertension or congestive heart failure in mammals, including man, comprising sequentially administering to a host suffering from hypertension or congestive heart failure a therapeutically acceptable amount of N"-cyano-N-4-pyridyl-N'-1,2,2-trimethylpropylguanidine and a therapeutically acceptable amount of a diuretic as specified in claim 1.

* * * * *